(12) United States Patent
Nair

(10) Patent No.: US 10,575,822 B2
(45) Date of Patent: Mar. 3, 2020

(54) DETECTING ENDOLEAKS ASSOCIATED WITH ANEURYSM REPAIR

(71) Applicant: VOLCANO CORPORATION, San Diego, CA (US)

(72) Inventor: Anuja Nair, Bedford, MA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 1139 days.

(21) Appl. No.: 14/594,763

(22) Filed: Jan. 12, 2015

(65) Prior Publication Data
US 2015/0196250 A1 Jul. 16, 2015

Related U.S. Application Data

(60) Provisional application No. 61/925,939, filed on Jan. 10, 2014, provisional application No. 61/925,996, filed on Jan. 10, 2014.

(51) Int. Cl.
*A61B 8/00* (2006.01)
*A61B 8/12* (2006.01)
(Continued)

(52) U.S. Cl.
CPC .............. *A61B 8/463* (2013.01); *A61B 5/026* (2013.01); *A61B 5/02014* (2013.01); *A61B 6/12* (2013.01);
(Continued)

(58) Field of Classification Search
CPC ......... A61B 8/463; A61B 5/026; A61B 6/487; A61B 5/02014; A61B 6/12; A61B 8/12; A61B 8/4416; A61B 8/5261; A61B 8/06
See application file for complete search history.

(56) References Cited

U.S. PATENT DOCUMENTS 7,105,020 B2 9/2006 Greenberg
8,298,147 B2 10/2012 Huennekens
(Continued)

FOREIGN PATENT DOCUMENTS

WO 2006076409 A2 7/2006

OTHER PUBLICATIONS

Hope, T.A. et al., "A comparison of flow patterns in ascending aortic aneurysms and volunteers using four-dimensional magnetic resonance velocity mapping", Proceedings of the Society for Magnetic resonance in Medicine. 2007, vol. 15, p. 247.
(Continued)

*Primary Examiner* — Joel Lamprecht

(57) ABSTRACT

The invention provides co-registration systems and methods for detecting endoleaks associated with aneurysm repair. The system includes an imaging device having expanded imaging capabilities and configured to capture and provide image data and flow visualization of a vessel based on the image data. The system further includes one or more sensors for capturing functional parameters of the vessel, such as flow or pressure. The system further includes an external imaging modality for capturing external image data of the vessel, such as, for example, a radiological image. The co-registration system is configured to co-register sets of data captured by a plurality of intra- and extraluminal modalities and provide a composite map (3- or multi-dimensional) of the vessel including automatically detected areas of interest, particularly during an EVAR or TEVAR procedure.

18 Claims, 12 Drawing Sheets

(51) Int. Cl.
*A61B 8/06* (2006.01)
*A61B 8/08* (2006.01)
*A61B 6/00* (2006.01)
*A61B 6/12* (2006.01)
*A61B 5/02* (2006.01)
*A61B 5/026* (2006.01)

(52) U.S. Cl.
CPC .............. *A61B 6/487* (2013.01); *A61B 8/06* (2013.01); *A61B 8/12* (2013.01); *A61B 8/4416* (2013.01); *A61B 8/5261* (2013.01)

(56) References Cited

U.S. PATENT DOCUMENTS

| | | | |
|---|---|---|---|
| 8,454,520 B2* | 6/2013 | Van Der Steen | A61B 8/481 600/407 |
| 8,568,326 B2 | 10/2013 | Smith | |
| 8,670,603 B2* | 3/2014 | Tolkowsky | A61B 5/0044 382/130 |
| 2002/0077546 A1 | 6/2002 | Aldefeld et al. | |
| 2004/0210118 A1 | 10/2004 | Letort | |
| 2006/0241465 A1* | 10/2006 | Huennekens | A61B 6/504 600/458 |
| 2008/0033302 A1 | 2/2008 | Grady et al. | |
| 2008/0033527 A1* | 2/2008 | Nunez | A61B 5/0215 623/1.13 |
| 2008/0269572 A1 | 10/2008 | Kanz et al. | |
| 2011/0071404 A1 | 3/2011 | Schmitt et al. | |
| 2014/0270436 A1* | 9/2014 | Dascal | G06T 7/11 382/130 |
| 2015/0196271 A1* | 7/2015 | Nair | A61B 8/06 600/439 |

OTHER PUBLICATIONS

Beebe, Hugh G. et al "Biplane Color Flow Duplex Intravenous Intravascular Ultrasound For Arterial Visualization", Journal Endovascular Surgery, vol. 5, 1998, pp. 101-105.

Beebe, H. et al., "Biplane Color Flow Duplex Intravenous Intravascular Ultrasound for Arterial Visualization", Journal of Endovascular Surgery, 1998.

* cited by examiner

DETECTING ENDOLEAKS ASSOCIATED WITH ANEURYSM REPAIR

CROSS-REFERENCE TO RELATED APPLICATION

This application claims the benefit of, and priority to, U.S. Provisional Patent Application Ser. No. 61/925,939, filed Jan. 10, 2014, and U.S. Provisional Patent Application Ser. No. 61/925,996, filed Jan. 10, 2014, the contents of each of which are incorporated by reference.

FIELD OF THE INVENTION

The present invention generally relates to evaluating cardiovascular health, and, more particularly, to methods for detecting endoleaks associated with aneurysm repair based on co-registered sets of data from a plurality of different intra- and extraluminal modalities.

BACKGROUND

An abdominal aortic aneurysm (AAA) is an abnormal swelling of the lower part of the aorta that extends through the abdominal area. The aorta is the primary blood vessel that transports blood from the heart to the rest of the body. The walls of aorta are elastic, which allow the vessel to be filled with blood under high pressure. An aneurysm occurs when the arterial walls become weakened and distended. Many factors can contribute to the weakening of arterial walls, including atherosclerosis, high cholesterol, hypertension, and smoking.

An aneurysm that has become too large may rupture, which is extremely dangerous. Symptoms of a ruptured aneurysm include excruciating pain of the lower back, flank, abdomen and groin. Bleeding associated with the rupture often leads to hypovolemic shock, and if left untreated, will result in a relatively quick death.

Conventional methods of repairing abdominal aortic aneurysms include surgical intervention and minimally invasive procedures like endovascular aneurysm repair (EVAR) and thoracic endovascular aneurysm repair (TEVAR). In the EVAR procedure, a stent graft (also known as an "endograft") is generally inserted into the aorta through small incisions in the groin. The stent graft reinforces the weakened part of the vessel from the inside and creates a new channel through which the blood flows, eliminating the risk of rupture at the site of the aneurysm. A primary concern associated with EVAR is that, despite placement of the stent graft, blood may continue to flow into the aneurysm, in what is commonly known as an endoleak. Endoleaks arising after grafting may be attributed to an incomplete sealing between the stent graft and the aortic wall or defects within the stent graft itself. Endoleaks are the major cause of complications in EVAR and TEVAR procedures, and thus failure in endoluminal treatment of AAA. When an endoleak occurs, it causes continued pressurization of the aneurysm sac and may leave the patient at risk of an AAA rupture and subsequently, immediate death.

Endoleaks are classified based on the origin of blood-leakage. There are generally five types of endoleaks (Type I through Type V). A type I endoleak is a perigraft leakage at proximal or distal stent graft attachment sites (near the renal and iliac arteries), a type II endoleak is a retrograde flow from collateral branches, such as the lumbar and inferior mesenteric arteries. A Type III endoleak is a leakage between overlapping parts of the stent (i.e. connection between overlapping components) or rupture through graft material and a type IV endoleak is leakage through the graft wall, generally due to the quality (porosity) of the graft material. A type V endoleak is generally expansion of the aneurysm sac without an identifiable leak (also called "endotension").

Type I and Type III leaks are considered to have high risk to the patient and must be identified and fixed during an EVAR/TEVAR procedure. A type I endoleak may be due to mal-apposition, or graft enfolding, of the stent graft at the proximal or distal landing zones (i.e., portions of the stent graft are not touching the luminal wall). A type III endoleak may be due to a damaged stent graft (e.g., hole in graft) or misaligned overlapping segments of the graft, causing a hole in the middle, hence, a leak. If either, or both, of these types of endoleaks are present, the aneurysm will continue to fill with blood and experience high pressure, leading to a high risk of rupture to the patient. As such, the identification and repair of these types of endoleaks is paramount to ensure patient safety and procedural success.

Currently, during EVAR/TEVAR procedures, physicians attempt to detect such leaks with existing imaging techniques, such as external imaging modalities (e.g., angiography, fluoroscopy, computed tomography (CT), and magnetic resonance imaging (MRI)). Based on the images, a physician may repair the leaks by correcting the graft-deployment, so as to ensure an appropriate seal. However, the use of non-invasive imaging techniques is restricted to either pre-procedural planning (CT and MRI) or peri-procedural monitoring with known limitations of the incidence-angle (angiography). Additionally, the use of external imaging techniques may be limiting and fail to provide the level of detail that intraluminal imaging techniques are able to offer. As such, the level of detection and monitoring of endoleaks may be sacrificed.

SUMMARY

The present invention provides systems and methods for detecting endoleaks associated with endovascular aneurysm repair based on a combination of intravascular images, extravascular images, and functional parameters, such as flow and pressure, of the vasculature. In one embodiment, a system is configured to co-register sets of data captured by a plurality of intra- and extravascular modalities and further provide a user, such as a surgeon, with an improved means of carrying out EVAR and/or TEVAR procedures based on the co-registered data. The system includes an imaging catheter having expanded imaging capabilities and being configured to acquire more than one form of image data related to the vessel and stent placed within, including structural data and intravascular flow data within the lumen. The system is configured to produce an intravascular image including at the least the structure and flow data, thereby providing flow visualization of a vessel. The system further includes one or more sensors for capturing functional measurements of the vessel, such as flow or pressure. The system further includes an external imaging modality for capturing external image data of the vessel, such as, for example, a radiological image.

The system is configured to co-register the intravascular image data, functional measurement data and extravascular image data of the vessel and reconfigure the co-registered data in a user friendly format to provide details related to the vessel. The details include, but not limited to, functional parameters of fluid within the vessel, characteristics of the vessel (e.g., dimensions), the location and characteristics of an interventional device, such as a stent graft, within the vessel, and the detection of endoleaks. The system is further configured to provide a composite map (3- or multi-dimensional) of the vessel including automatically detected areas of interest (e.g., high stress/strain maps, endoleaks, atherosclerosis, thrombus, dissection, etc.), particularly during an EVAR or TEVAR procedure.

The system is configured to provide automated detection and identification of different types of endoleaks (Types I through Type V) based on at least flow visualization from the captured image data, as well as detected characteristics of the stent graft. In particular, the flow within a lumen can be visualized by a particular color or a pattern of colors corresponding to a particular attribute of the flow (e.g. motion or speed of the flow, direction of the flow, etc.). The system may include the use of phased array imaging, Doppler based signaling, and/or other cross-correlation algorithm used for detecting a change, or a flow pattern, in a series of image and flow data captured by the imaging catheter or probe. Additionally, or alternatively, the flow visualization could also be enhanced by use of a contrast material for ultrasound or ultrasound-activated micro bubbles offering flow contrast.

In addition, an imaging catheter or probe consistent with the present invention is configured to capture intravascular image data via ultrasound at a frequency sufficient to provide an adequate field-of-view of the vascular walls and surrounding tissues. For example, in one embodiment, the imaging catheter is configured to capture the intravascular image data via ultrasound at a frequency between at least 9 MHz and 11 MHz, so as to provide near 360 degree tomographic views of the vascular walls from within the vessel. Accordingly, the imaging catheter consistent with the present disclosure is configured to capture image data providing adequate field-of-view of the large aorta, for example.

Systems and methods of the present invention will improve interventional evaluation by providing a physician with critical information about flow and structure while also reducing the time for procedures. In particular, the addition of flow visualization capability to IVUS, as well as accurate functional measurements, can significantly improve the detection of endoleaks. More specifically, IVUS can provide accurate measurements in sizing and assessing stent graft landing zones, which is generally more accurate than the traditional external imaging modalities (e.g., angiography, CT, MRI, etc.) alone. Additionally, the inclusion of external image data, such as an angiogram, with IVUS and functional measurement data, further provides crucial information on vessel tortuosity that is otherwise unavailable from IVUS alone. Furthermore, use of angiography may allow surgeons to plan the EVAR/TEVAR procedure in identifying AAA neck angulation, which aids in the selection of the appropriate stent graft for that patient.

Finally, with the inclusion of functional measurements, a surgeon may utilize pressure and/or flow variations from intra-aneurysmal-sac and intra-luminal spaces to further confirm and improve accuracy of detecting endoleaks. The use of functional measurements alone, without angiography and/or IVUS, is generally insufficient to distinguish between the different types of leaks. Accordingly, the combination of all the different types of data (e.g., intravascular imaging data, extravascular imaging data, and functional measurements) provides a comprehensive evaluation of a vessel. Accordingly, the system is useful in the various clinical scenarios, such as use for identifying vascular dissections and true lumen (to ensure stents and grafts are deployed in the true lumen), detection of thrombus in the lumen at the site of an AAA, as well as venous thrombus identification within.

Systems and methods of the invention are useful in verifying the effectiveness of EVAR/TEVAR procedures. Exclusion of the aneurysm sac is the main goal of the stent graft treatment, and clinical success is defined by the "total exclusion" of the aneurysm. By confirming the absence of endoleaks using the provided methods, the aneurysm can be deemed to have been totally excluded. In addition, the early detection of endoleaks, as well as the type of endoleak, at the time of surgery (perioperatively) can avoid complications at a later time and decrease patient mortality.

DETAILED DESCRIPTION

Figure 1:
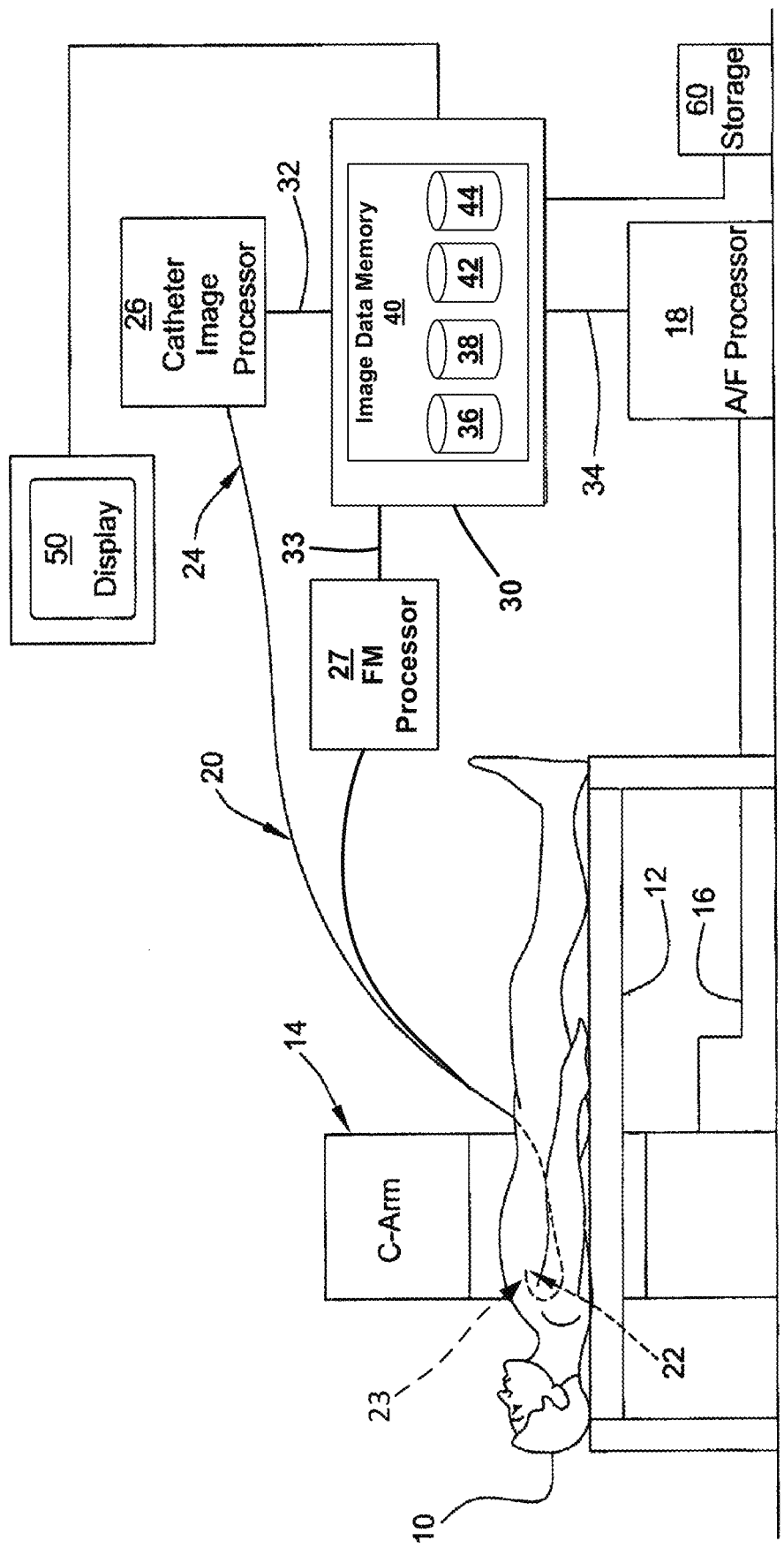
FIG. 1 is a schematic illustration of a system for implementing multiple modality co-registration consistent with the present disclosure.

The present invention is a co-registration system configured to co-register sets of data captured by a plurality of intra- and extravascular modalities and for the detection of endoleaks associated with endovascular aneurysm repair. By way of overview, the system generally includes an imaging catheter having expanded imaging capabilities and being configured to acquire more than one form of image data related to the vessel and stent placed within, including structural data and intravascular flow data within the lumen.

The system is configured to produce an intravascular image including at the least the structure and flow data, thereby providing flow visualization of a vessel. The system further includes one or more sensors for capturing functional measurements of the vessel, such as flow or pressure. The system further includes an external imaging modality for capturing external image data of the vessel, such as, for example, a radiological image.

The system is configured to co-register the intravascular image data, functional measurement data and extravascular image data of the vessel and reconfigure the co-registered data in a user friendly format to provide details related to the vessel. The details include, but are not limited to, functional parameters of fluid within the vessel, characteristics of the vessel (e.g., dimensions), the location and characteristics of an interventional device, such as a stent graft, within the vessel, and the detection of endoleaks. The system is further configured to provide a composite map (3- or multi-dimensional) of the vessel including automatically detected areas of interest (e.g., high stress/strain maps, endoleaks, atherosclerosis, thrombus, dissection, etc.), particularly during an EVAR or TEVAR procedure.

Systems and methods of the present invention will improve interventional evaluation by providing a physician with critical information about flow and structure while also reducing the time for procedures. In particular, the addition of flow visualization capability to IVUS, as well as accurate functional measurements, can significantly improve the detection and classification of endoleaks. More specifically, IVUS can provide accurate measurements in sizing and assessing stent graft landing zones, which is generally more accurate than the traditional external imaging modalities (e.g., angiography, CT, MRI, etc.) alone. Additionally, the inclusion of external image data, such as an angiogram, with IVUS and functional measurement data, further provides crucial information on vessel tortuosity that is otherwise unavailable from IVUS alone. Furthermore, use of angiography may allow surgeons to plan the EVAR/TEVAR procedure in identifying AAA neck angulation, which aids in the selection of the appropriate stent graft for that patient.

Finally, with the inclusion of functional measurements, a surgeon may utilize pressure and/or flow variations from intra-aneurysmal-sac and intra-luminal spaces to further confirm and improve accuracy of detecting endoleaks. Functional measurements alone, without angiography and/or IVUS, are generally insufficient to distinguish between the different types of leaks. Accordingly, the combination of all the different types of data (e.g., intravascular imaging data, extravascular imaging data, and functional measurements) provides a comprehensive evaluation of a vessel. Accordingly, the system is useful in the various clinical scenarios, such as use for identifying vascular dissections and true lumen (to ensure stents and grafts are deployed in the true lumen), detection of thrombus in the lumen at the site of an AAA, as well as venous thrombus identification within.

Turning to FIG. 1, an exemplary system is schematically depicted for carrying out the present invention in the form of co-registration of angiogram/fluoroscopy, intravascular ultrasound images, and functional measurement data. The radiological and ultrasound image data acquisition subsystems are generally well known in the art. With regard to the radiological image data, a patient 10 is positioned upon an angiographic table 12. The angiographic table 12 is arranged to provide sufficient space for the positioning of an angiography/fluoroscopy unit c-arm 14 in an operative position in relation to the patient 10 on the table 12. Radiological image data acquired by the angiography/fluoroscopy c-arm 14 passes to an angiography/fluoroscopy (A/F) processor 18 via transmission cable 16. The angiography/fluoroscopy processor 18 converts the received radiological image data received via the cable 16 into angiographic/fluoroscopic image data. The angiographic/fluoroscopic ("radiological") image data is initially stored within the processor 18.

With regard to portions of the system associated with acquiring ultrasound image data, an imaging catheter 20, such as an IVUS catheter, is inserted within the patient 10 so that its distal end, including a diagnostic probe 22 (in particular an IVUS probe), is in the vicinity of a desired imaging location of a blood vessel. While not specifically identified in FIG. 1, a radiopaque material located near the probe 22 provides indicia of a current location of the probe 22 in a radiological image. By way of example, the diagnostic probe 22 generates ultrasound waves, receives ultrasound echoes representative of a region proximate the diagnostic probe 22, and converts the ultrasound echoes to corresponding electrical signals. The corresponding electrical signals are transmitted along the length of the imaging catheter 20 to a proximal connector 24. IVUS versions of the probe 22 come in a variety of configurations including single and multiple transducer element arrangements. In the case of multiple transducer element arrangements, an array of transducers is potentially arranged: linearly along a lengthwise axis of the imaging catheter 20, curvilinearly about the lengthwise axis of the catheter 20, circumferentially around the lengthwise axis, etc.

The proximal connector 24 of the catheter 20 is communicatively coupled to a catheter image processor 26. The catheter image processor 26 converts the signals received via the proximal connector 24 into, for example, cross-sectional images of vessel segments. Additionally, the catheter image processor 26 generates longitudinal cross-sectional images corresponding to slices of a blood vessel taken along the blood vessel's length. The IVUS image data rendered by the catheter image processor 26 is initially stored within the processor 26.

The type of diagnostic imaging data acquired by the diagnostic probe 22 and processed by the catheter image processor 26 varies in accordance with alternative embodiments of the invention. In accordance with a particular alternative embodiment, the diagnostic probe 22 is equipped with one or more sensors (e.g., Doppler and/or pressure) for providing hemodynamic information (e.g., blood flow velocity and pressure)—also referred to as functional flow measurements. In such alternative embodiments, functional flow measurements are processed by the catheter image processor 26. It is thus noted that the term "image" is intended to be broadly interpreted to encompass a variety of ways of representing vascular information including blood pressure, blood flow velocity/volume, blood vessel cross-sectional composition, shear stress throughout the blood, shear stress at the blood/blood vessel wall interface, etc.

In the case of acquiring hemodynamic data for particular portions of a blood vessel, effective diagnosis relies upon the ability to visualize a current location of the diagnostic probe 22 within a vasculature while simultaneously observing functional flow metrics indicative of cardiovascular disease. Co-registration of hemodynamic and radiological images facilitates precise treatment of diseased vessels. Alternatively, instead of catheter mounted sensors, the sensors can be mounted on a guidewire, for example a guidewire with a diameter of 0.018" or less or more. Thus, in accordance with embodiments of the present invention, not only are a variety of probe types used, but also a variety of flexible elongate members to which such probes are mounted at a distal end (e.g., catheter, guidewire, etc.).

The catheter 20, including the diagnostic probe 22, may have expanded imaging capabilities, including flow visualization capabilities. For example, the image processor 26 may be configured to process image data captured by the diagnostic probe 22 and cause relevant information, such as flow, to be displayed, thereby providing flow visualization. In one embodiment, the system may include an intravascular ultrasound (IVUS) catheter 20 including an imaging probe 22 having one or more ultrasound transducers, wherein the imaging probe can be introduced into a vessel and maneuvered to site where the stent graft was placed. Once positioned, the imaging probe can collect the appropriate data, which can then be used to discern the presence of endoleaks, automatically or visually by the operator. For instance, the ultrasound transducers are configured to acquire more than one form of data related to the vessel and stent placed within. The system is configured to produce an intravascular image that includes not only structure data of the lumen, but further includes intravascular flow data within the lumen, particularly within the site where the stent graft was placed. Accordingly, the system may include the catheter and image processing methods described in co-pending U.S. application Ser. No. 14/594,599, filed Jan. 12, 2015, the contents of which are incorporated herein by reference in their entirety.

Furthermore, one or more sensors for capturing functional measurements may be inserted within the patient. For example, a functional measurement device 23 may be inserted within the patient 10, generally in the vicinity of a desired imaging location of a blood vessel. The functional measurement device 23 may be equipped with a pressure sensor, a flow sensor, or any combination thereof. Exemplary functional measurement devices suitable for use in practicing the invention include FloWire Doppler Guidewire and the ComboWire XT Guidewire by Volcano Corporation. In particular embodiments, a pressure sensor can be mounted on the distal portion of the catheter 20, for example. Additionally, or alternatively, the pressure sensor can be mounted to a separate catheter or guidewire. Additional details of suitable pressure sensors that may be used with devices of the invention are described in U.S. Pat. No. 6,106,476. A flow sensor can be used to measure blood flow velocity within the vessel, which can be used to assess coronary flow reserve (CFR). The flow sensor can be, for example, an ultrasound transducer, a Doppler flow sensor or any other suitable flow sensor, disposed at or in close proximity to the distal tip of the guidewire. The ultrasound transducer may be any suitable transducer, and may be mounted in the distal end using any conventional method, including the manner described in U.S. Pat. Nos. 5,125,137, 6,551,250 and 5,873,835.

A pressure sensor allows one to obtain pressure measurements within a body lumen. A particular benefit of pressure sensors is that pressure sensors allow one to measure of fractional flow reserve (FFR) in vessel. FFR is a comparison of the pressure within a vessel at positions prior to the stenosis and after the stenosis. The level of FFR determines the significance of the stenosis, which allows physicians to more accurately identify clinically relevant stenosis. For example, an FFR measurement above 0.80 indicates normal coronary blood flow and a non-significant stenosis. Another benefit is that a physician can measure the pressure before and after an intraluminal intervention procedure to determine the impact of the procedure.

The functional measurement device 23 is coupled to a functional measurement (FM) processor 27. The FM processor 27 is configured to receive the signals transmitted from the device 23 and further convert the signals into, for example, functional measurement data that can be graphically displayed to illustrate the data captured by the FM device 23. The functional measurement data rendered by the FM processor 27 may be initially stored within the processor 27.

A co-registration processor 30 receives IVUS image data from the catheter image processor 26 via line 32, functional measurement data from the FM processor 27 via line 33, and radiological image data from the radiological image processor 18 via line 34. Alternatively, the communications between the sensors and the processors are carried out via wireless media. The co-registration processor 30 renders a co-registration image including, functional measurement data, radiological, and IVUS image frames derived from the received image data.

In accordance with one embodiment of the present invention, indicia (e.g., a radiopaque marker artifact) are provided on the radiological images of a location corresponding to simultaneously displayed IVUS image data. The co-registration processor 30 initially buffers angiogram image data received via line 34 from the radiological image processor 18 in a first portion 36 of image data memory 40. Thereafter, during the course of a catheterization procedure, IVUS and radiopaque marker image data received via lines 32 and 34 is stored within a second portion 38 and a third portion 42, respectively, of the image data memory 40. In addition to IVUS and radiopaque marker image data, hemodynamic data (e.g., functional measurement data) may be acquired by the FM device 23 during the course of a catheterization procedure. Accordingly, functional measurement data received via line 33 is stored within a fourth portion 44 of the image data memory. The individually rendered frames of stored image data, as well as the functional measurement data, are appropriately tagged (e.g., time stamp, sequence number, etc.) to correlate IVUS image frames and corresponding radiological (radiopaque marker) image data frames, as well as functional measurement data. In other embodiments, only IVUS data may be acquired (while hemodynamic data is not acquired), or vice versa.

The co-registration processor 30 renders a co-registration image from the data previously stored within the first portion 36, second portion 38, third portion 42, and/or fourth portion 44 of the image data memory 40. By way of example, a particular IVUS image frame/slice is selected from the second portion 38. The co-registration processor 30 is configured to identify fluoroscopic image data within the third portion 42 and/or functional measurement data within the fourth portion 44 corresponding to the selected IVUS image data from the second portion 38. Thereafter, the co-registration processor 30 is configured to superimpose or co-aligns the fluoroscopic image data from the third portion 42 and/or functional measurement data from the fourth portion 44 with the angiogram image frame retrieved from the first portion 36. Thereafter, the co-registered radiological and IVUS image frames, and or functional measurement data, are simultaneously displayed, along-side one another, upon a graphical display device 50. The co-registered frames driving the display device 50 are also stored upon a long-term storage device 60 for later review.

As generally understood, the system depicted in FIG. 1 may be used to perform on a patient any number of medical sensing procedures such as intravascular ultrasound (IVUS), angiography, virtual histology (VH), forward looking IVUS (FL-IVUS), intravascular photoacoustic (IVPA) imaging, a fractional flow reserve (FFR) determination, a coronary flow reserve (CFR) determination, optical coherence tomography (OCT), computed tomography (CT), intracardiac echocardiography (ICE), forward-looking ICE (FLICE), intravascular palpography, transesophageal ultrasound (TEE), thermography, magnetic resonance imaging (MRI), micro-magnetic resonance imaging (mMRI or µMRI), or any other medical sensing modalities known in the art. Further, the system may be used to perform one or more treatment or therapy procedures on a patient such as radiofrequency ablation (RFA), cryotherapy, atherectomy or any other medical treatment procedure known in the art.

Any target can be imaged by methods and systems of the invention including, for example, bodily tissue. In certain embodiments, systems and methods of the invention image structural information and movement or flow within a lumen of tissue. Various lumen of biological structures may be imaged including, but not limited to, blood vessels, vasculature of the lymphatic and nervous systems, various structures of the gastrointestinal tract including lumen of the small intestine, large intestine, stomach, esophagus, colon, pancreatic duct, bile duct, hepatic duct, lumen of the reproductive tract including the vas deferens, vagina, uterus and fallopian tubes, structures of the urinary tract including urinary collecting ducts, renal tubules, ureter, and bladder, and structures of the head and neck and pulmonary system including sinuses, parotid, trachea, bronchi, and lungs.

Figure 2:
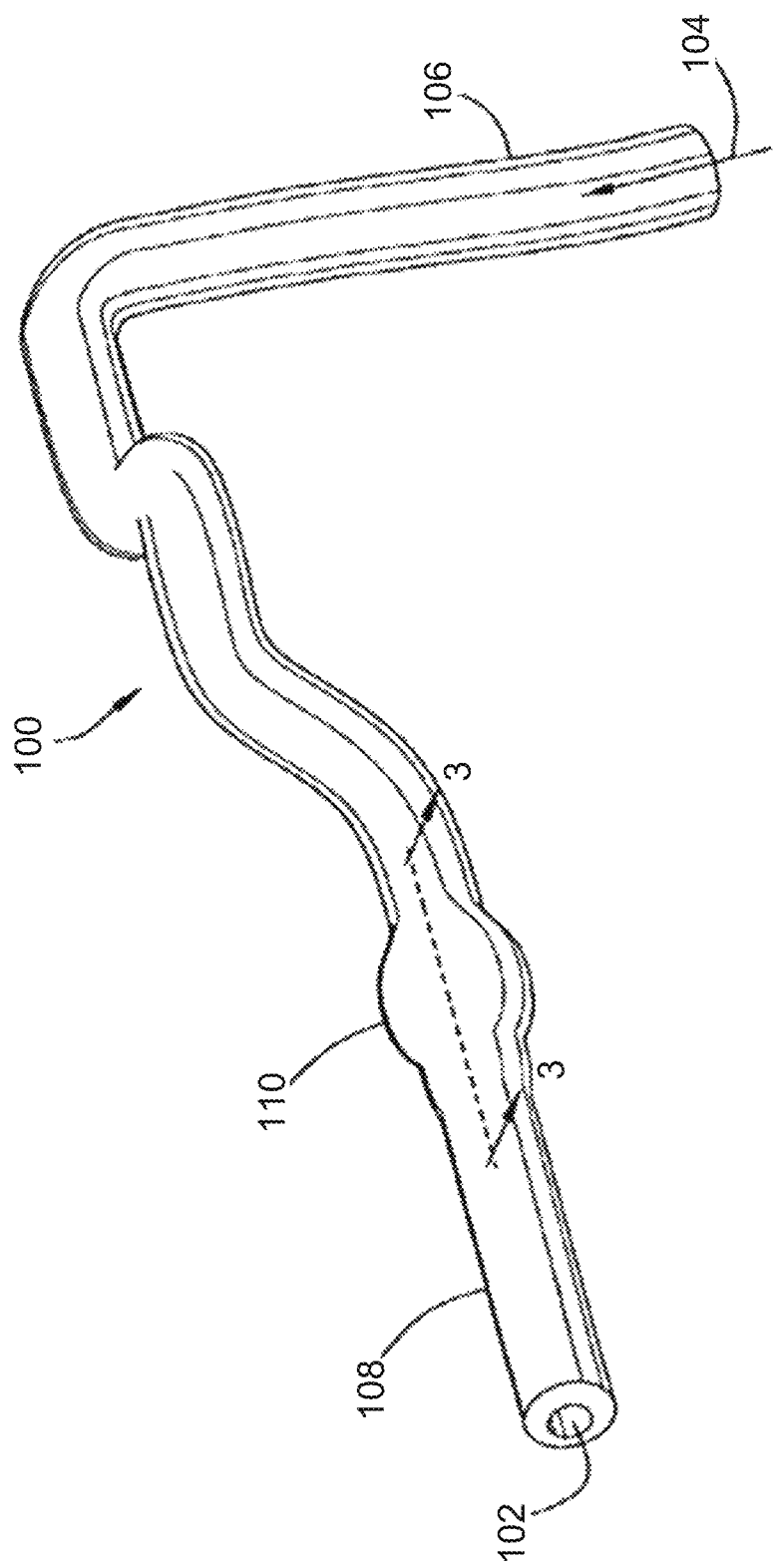
FIG. 2 is a graphical illustration of a three dimensional length of artery, including a highly diseased segment.
Figure 3:
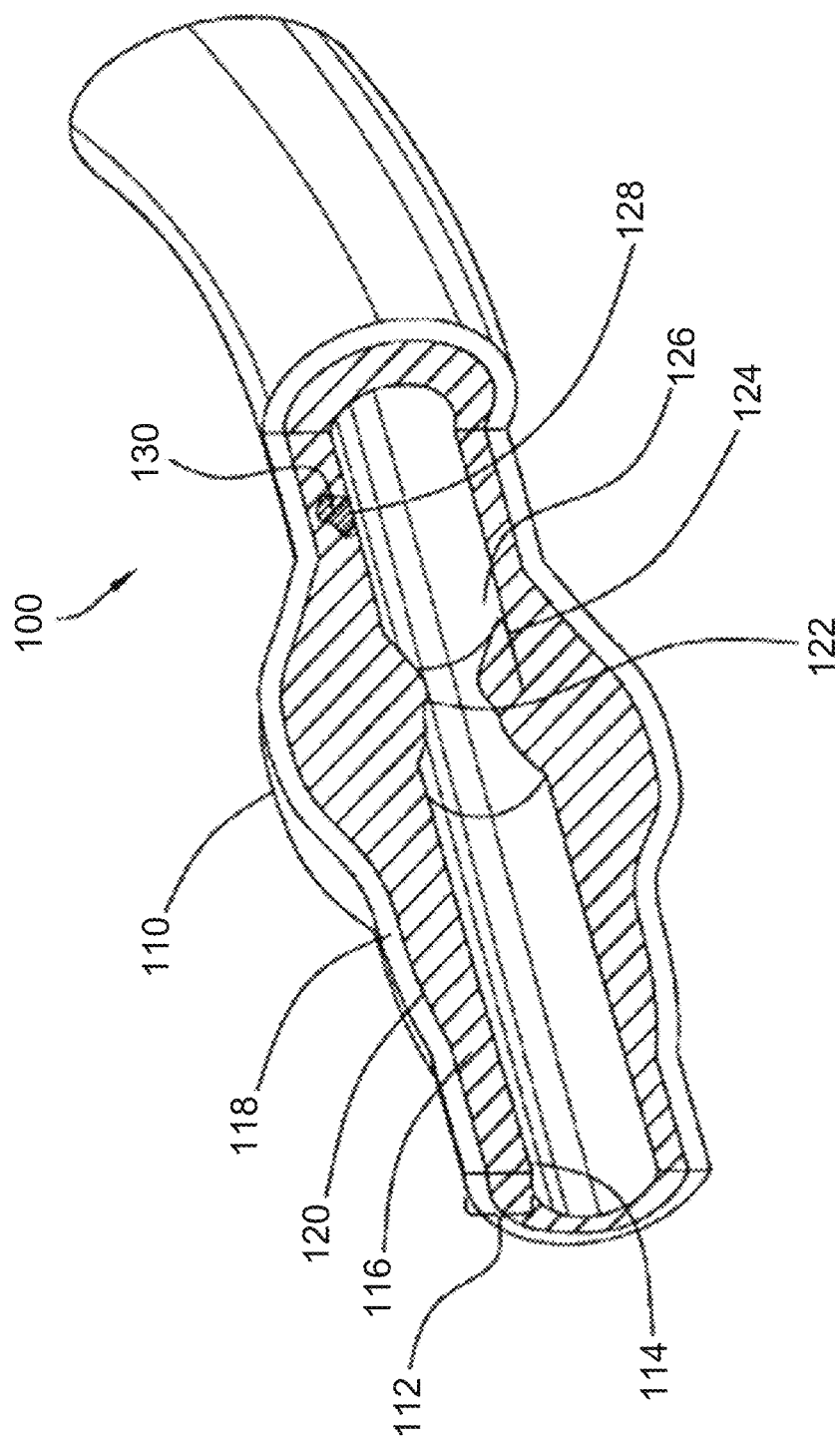
FIG. 3 is a graphical illustration of a portion of the artery depicted in FIG. 2 with a longitudinal section removed along lines 3 to illustratively depict different elements of atherosclerotic plaque.

FIG. 2 is a graphical illustration of a three dimensional length of artery 100, including a highly diseased segment. In FIG. 2, a diseased artery 100 with a lumen 102 is shown. Blood flows through the artery 100 in a direction indicated by arrow 104 from proximal end 106 to distal end 108. A stenotic area 110 is seen in the artery 100. FIG. 3 shows a sectioned portion of the stenotic area 110 of the artery 100. An artery wall 112 consists of three layers, an intima 114, a media 116 and an adventitia 118. An external elastic lamina (EEL) 120 is the division between the media 116 and the adventitia 118. A stenosis 122 is located in the artery 100 and limits blood flow through the artery 100. A flap 124 is shown at a high stress area 126 of the artery 100. Proximal to the stenosis 122 is an area of vulnerability 128, including a necrotic core 130 which is very close to the lumen. A rupture commonly occurs in an area such as the area of vulnerability 128.

Figure 4:
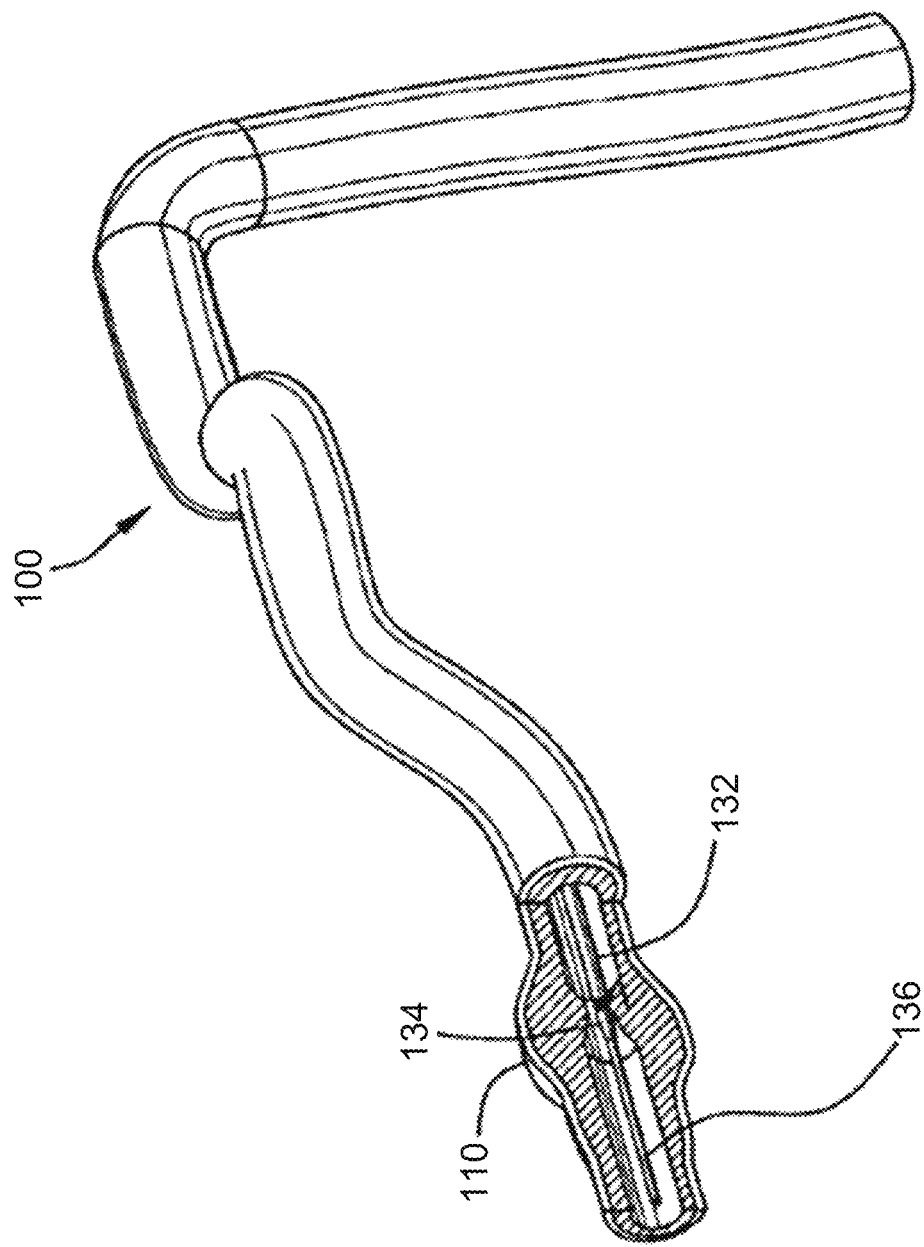
FIG. 4 is a graphical illustration of the artery from FIGS. 2 and 3 wherein an imaging catheter consistent with the present disclosure has been inserted in the artery.
Figure 5:
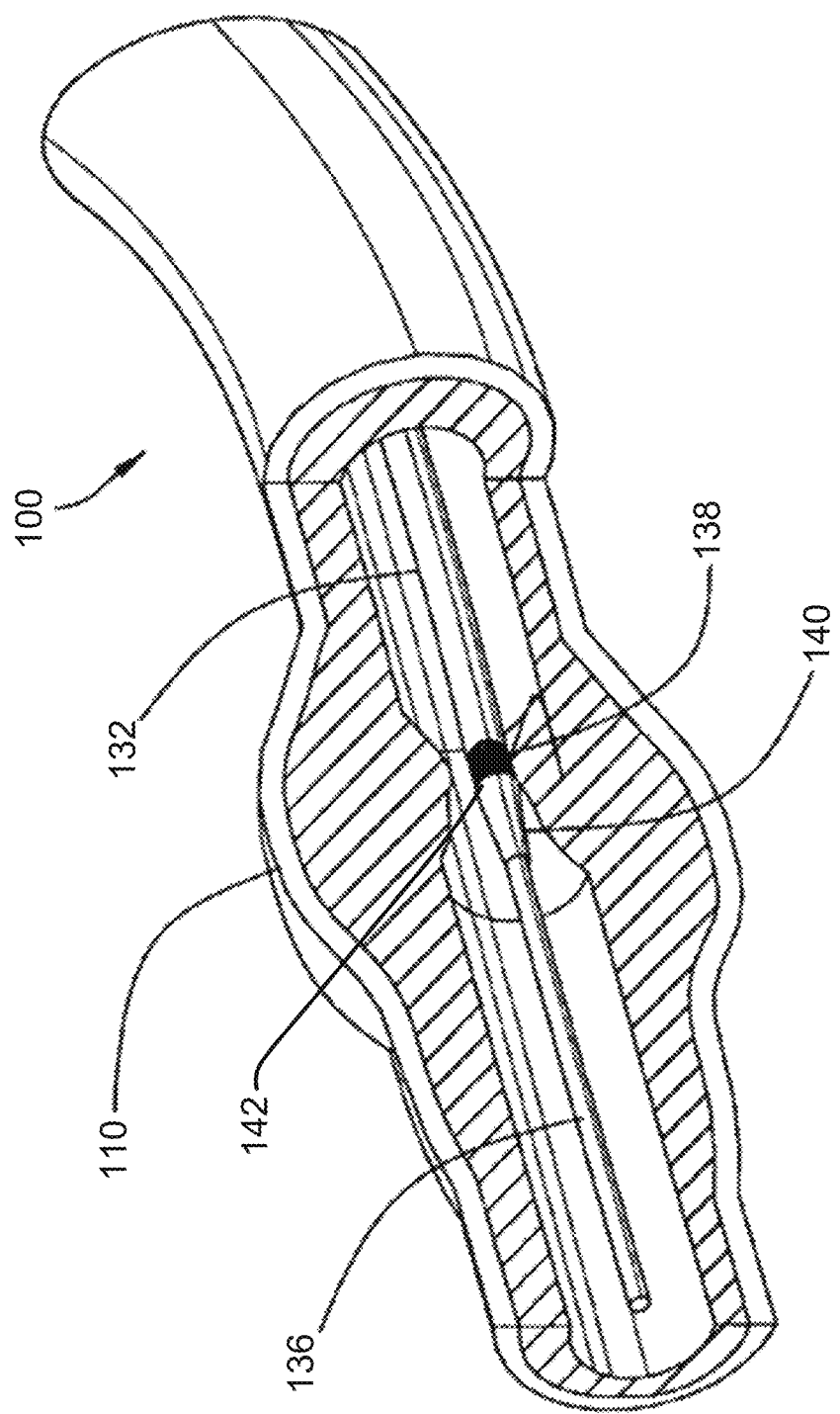
FIG. 5 is detailed view of a section of the artery depicted in FIG. 4 including the imaging catheter in the artery.

FIG. 4 illustratively depicts an imaging catheter 132 having a distal end 134 that is inserted into the stenotic area 110 of the artery 100. In some embodiments, the imaging catheter 132 is inserted over a guidewire 136, which allows the imaging catheter 132 to be steered to the desired location in the artery 100. As depicted in FIG. 5, the imaging catheter 132 includes an imaging sensor 138 for imaging the diseased portions and normal portions of the artery 100. The imaging sensor 138 is, for example, a rotating ultrasound transducer, an array of ultrasound transducer elements such as phased array/cMUT, an optical coherence tomography (OCT) probe, a spectroscopy probe, angioscopy, or other type of imaging sensor for capturing endoluminal image data.

As mentioned previously, in some embodiments, the imaging assembly is an IVUS imaging assembly. The imaging assembly can be a phased array IVUS imaging assembly, a single transducer rotating type IVUS imaging assembly, or an IVUS imaging assembly that uses photoacoustic materials to produce diagnostic ultrasound and/or receive reflected ultrasound for diagnostics. IVUS imaging assemblies and processing of IVUS data are described for example in Yock, U.S. Pat. Nos. 4,794,931, 5,000,185, and 5,313,949; Sieben et al., U.S. Pat. Nos. 5,243,988, and 5,353,798; Crowley et al., U.S. Pat. No. 4,951,677; Pomeranz, U.S. Pat. No. 5,095,911, Griffith et al., U.S. Pat. No. 4,841,977, Maroney et al., U.S. Pat. No. 5,373,849, Born et al., U.S. Pat. No. 5,176,141, Lancee et al., U.S. Pat. No. 5,240,003, Lancee et al., U.S. Pat. No. 5,375,602, Gardineer et al., U.S. Pat. No. 5,373,845, Seward et al., Mayo Clinic Proceedings 71(7): 629-635 (1996), Packer et al., Cardiostim Conference 833 (1994), "Ultrasound Cardioscopy," Eur. J.C.P.E. 4(2):193 (June 1994), Eberle et al., U.S. Pat. No. 5,453,575, Eberle et al., U.S. Pat. No. 5,368,037, Eberle et al., U.S. Pat. No. 5,183,048, Eberle et al., U.S. Pat. No. 5,167,233, Eberle et al., U.S. Pat. No. 4,917,097, Eberle et al., U.S. Pat. No. 5,135,486, and other references well known in the art relating to intraluminal ultrasound devices and modalities. All of these references are incorporated by reference herein in their entirety.

As previously described herein, the imaging catheter 132 and imaging sensor 138 may have flow visualization capabilities, wherein the imaging sensor 138 is configured to operate in more than one mode to collect different sets of data related to a vessel, including structural data and intravascular flow data to produce an IVUS image including structure and flow data of the vessel. Accordingly, the system may include the catheter and image processing methods described in U.S. Provisional Patent Ser. No. 61/925,939, filed Jan. 10, 2014 (included herewith in Appendix A), the contents of which are incorporated herein by reference in their entirety.

As shown in FIG. 5, distal to the imaging sensor 138 is a tapered tip 140 which allows the imaging catheter 132 to easily track over the guidewire 136, especially in challenging tortuous, stenotic or occluded vessels. In other embodiments, the tapered tip 140 may be closed end. Once introduced to a site-of-interest, the imaging catheter 132 can be pulled back over a desired length of the vessel, obtaining imaging information along this desired length, and thereafter creating a volumetric model of the vessel wall, including the diseased and normal portions, from a set of circumferential cross-section images obtained from the imaging information. Some technologies, such as IVUS, allow for the imaging of flowing blood and thrombus. Furthermore, the catheter 132 may include one or more functional measurement devices 142 positioned at or near the distal end.

The co-registration system of FIG. 1, including the imaging catheter 20, 132, functional measurement device 23, 142, and angiography device 14, may be used to detect, and further identify, endoleaks associated with aneurysm repair procedures, such as EVAR or TEVAR procedures. Reference will now be made to endovascular aneurysm repair (EVAR) procedure. Methods of the invention are useful with all EVAR related procedures, including without limitation, EVAR, hybrid EVAR, Common Iliac Artery EVAR, and Thoracic EVAR (TEVAR).

Figure 6:
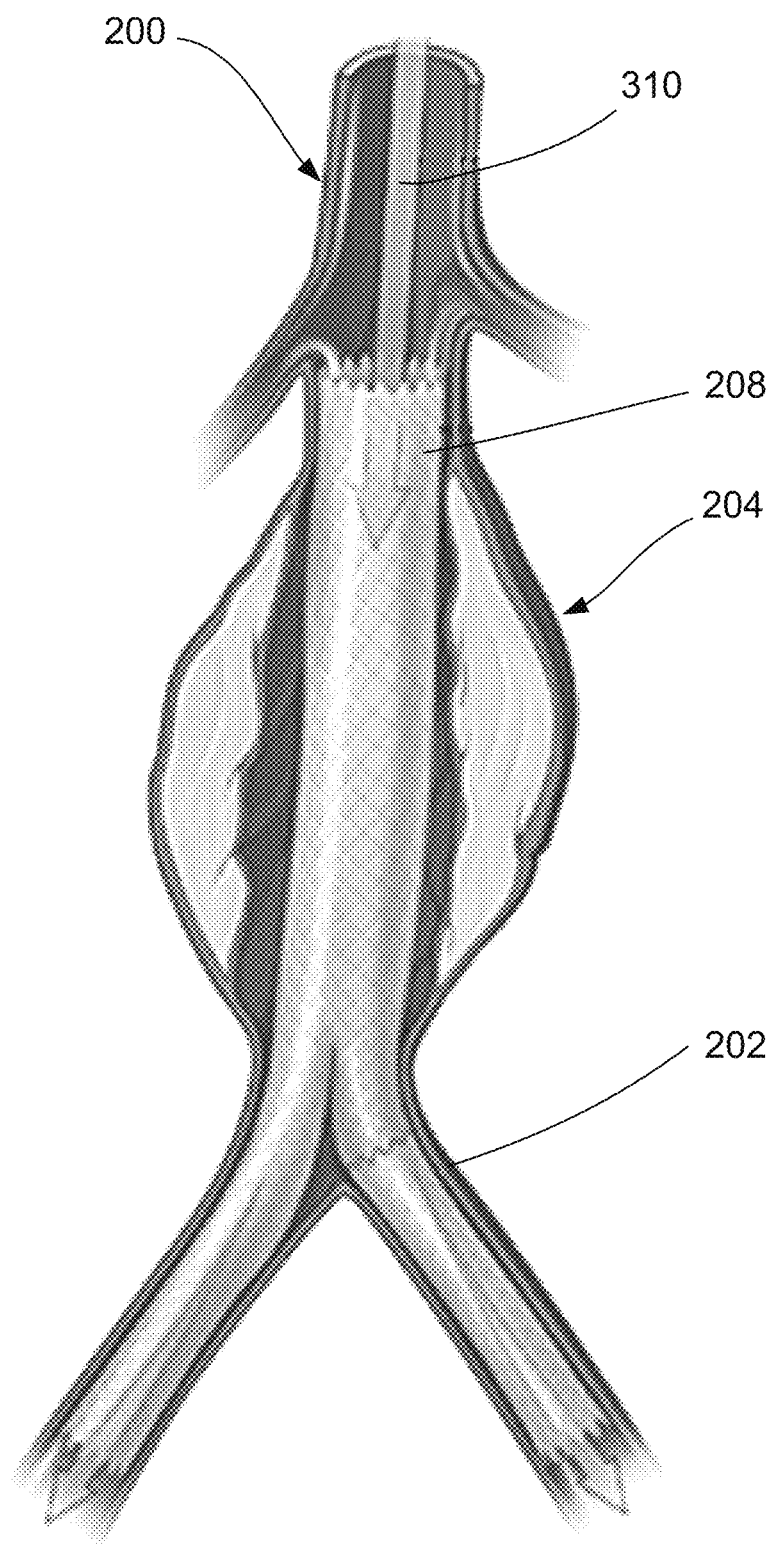
FIG. 6 is a cross-sectional view of a portion of an aorta illustrating placement of stent graft at an abdominal aortic aneurysm (AAA) site during an EVAR procedure.

FIG. 6 is a cross-sectional view of a portion of an aorta 200 illustrating placement of stent graft 208 at an abdominal aortic aneurysm (AAA) site 204 during an EVAR procedure. EVAR is typically conducted in a sterile environment, usually a theatre, under x-ray fluoroscopic guidance. The patient is usually administered an anesthetic prior to conducting the procedure. A puncture is then made with a needle in the femoral artery 202 of the groin. An introducer or vascular sheath is then inserted into the artery with a large needle, and after the needle is removed, the introducer provides access for guidewires, catheters, and other endovascular tools, such as the stent graft 308 used to treat the abdominal aneurysm 202. As shown, once in place, the stent graft 208 acts as an artificial lumen for blood to flow through, as indicated by arrow 210, and not into the surrounding aneurysm sac 204. This reduces the pressure in the aneurysm 204, which itself will usually thrombose and shrink in size over time.

Diagnostic angiography images or 'runs' of the aorta are captured to determine the location of the patient's renal arteries, so the stent graft can be deployed without blocking them. Blockage may result in renal failure, thus the precision and control of the graft stent deployment is extremely important. The main 'body' of the stent graft is placed first, follow by the 'limbs' which join on to the main body and sit on the Aortic Bifurcation for better support, and extend to the Iliac arteries. The stent graft (covered stent), once positioned, serves as an artificial lumen for blood to flow down, and not into the surrounding aneurysm sac. Accordingly, pressure is taken off the aneurysm wall, which itself will thrombose in time.

For certain occasions that the aneurysm extends down to the Common Iliac Arteries, a specially designed graft stent, named as Iliac Branch Device (IBD), can be used, instead of blocking the Internal Iliac Arteries, but to preserve them. The preservation of the Internal Iliac Arteries is important to prevent Buttock Claudication, and to preserve the full genital function.

A variation of EVAR is the Hybrid Procedure. A hybrid procedure occurs in the angiography room and aims to combine endovascular procedures with limited open surgery. In this procedure the stent graft deployment is planned to combine with an open operation to revascularise selected arteries that will be "covered" by the stent graft i.e. deprived of arterial inflow. In this method more extensive EVAR devices can be deployed to treat the primary lesion while preserving arterial flow to critical arteries.

Thoraco-abdominal aneurysms (TAA) typically involve such vessels and deployment of the EVAR device will cover important arteries e.g. visceral or renal arteries, resulting in end organ ischemia which may not be survivable. The open operation component aims to bring a bypass graft from an artery outside the stent graft coverage to vital arteries within the coverage region. This component adds to the EVAR procedure in time and risk but is usually judged to be lesser that the risk of the major totally open operation.

The above procedures aim to reduce the morbidity and mortality of treating certain types of arterial disease. The occurrence of endoleaks, however, can significantly increase the risk associated with EVAR procedures. An endoleak is characterized by persistent blood flow within the aneurysm sac following endovascular aneurysm repair. Normally the aortic stent graft used for EVAR excludes the aneurysm from the circulation by providing a conduit for blood to bypass the sac. An improperly positioned or defective graft, however, can result in an ineffectual seal and result in the formation of endoleaks.

An endoleak is a common complication of EVAR and is found in a significant number of patients intraoperatively (seen on the on-table angiogram after stent deployment), as well as during follow-up. This somewhat common occurrence greatly reduces the overall effectiveness of the EVAR procedure. Although some endoleaks appear to be unavoidable due to the presence of pre-existing patent branch vessels arising from the aneurysm sac, others occur as a result of poor graft selection.

In either situation, there is an immediate need to monitor the occurrence of endoleaks, preferably during the procedure itself (perioperatively). Systems and methods of the invention address this need and can be used perioperatively. While the patient is still on the operating table and has the introducer used for delivering the stent graft still inside him, the same introducer can be used to maneuver the imaging catheter 132 and imaging sensor 138 to the site of the implanted graft and acquire image data near the site of implantation to further provide flow visualization as well as functional measurement data via the functional measurement device 142 for the detection and characterization of endoleaks.

Endoleaks are typically classified as type I, type II, type III, type IV, and type V endoleaks.

Type I endoleaks occur as a result of an inadequate seal at the site of the graft attachment. It may occur at the proximal end or distal end. Blood flow leaks alongside the graft into the aneurysm sac. They are often the result of unsuitable patient (aneurysm) selection or device selection for the EVAR procedure, but can also occur if the graft migrates. Type I leaks are always considered significant as they do not tend to resolve spontaneously.

Type II endoleaks are the most common. In this situation, retrograde flow though branch vessels continues to fill the aneurysm sac. The most common culprit vessels are lumbar arteries, inferior mesenteric artery or internal iliac artery. This type of leak has been a substantial number of cases. It usually resolves spontaneously over time and requires no treatment. Embolization of the branch vessel is indicated if the aneurysm sac continues to expand in size.

Type III endoleaks are caused by mechanical failure of the stent graft. There may be a fracture of the stent graft, hole or defect on the graft fabric, or junctional separation of the modular components. Causes may relate to defective device material, extreme angulation of a segment predisposing to fracture, or improper overlap of the modular components during insertion.

Type IV endoleaks occur when blood leaks across the graft due to its porosity. It does not require any treatment and typically resolves within a few days of graft placement.

Type V "leak" (also referred to as endotension) is not a true leak but is defined as continued expansion of the aneurysm sac without evidence of a leak site. It is also referred to as endotension. Its origin is still unclear but is believed to be due to pulsation of the graft wall with transmission of the pulse wave through the perigraft space (aneurysm sac) to the native aneurysm wall.

Figure 7:
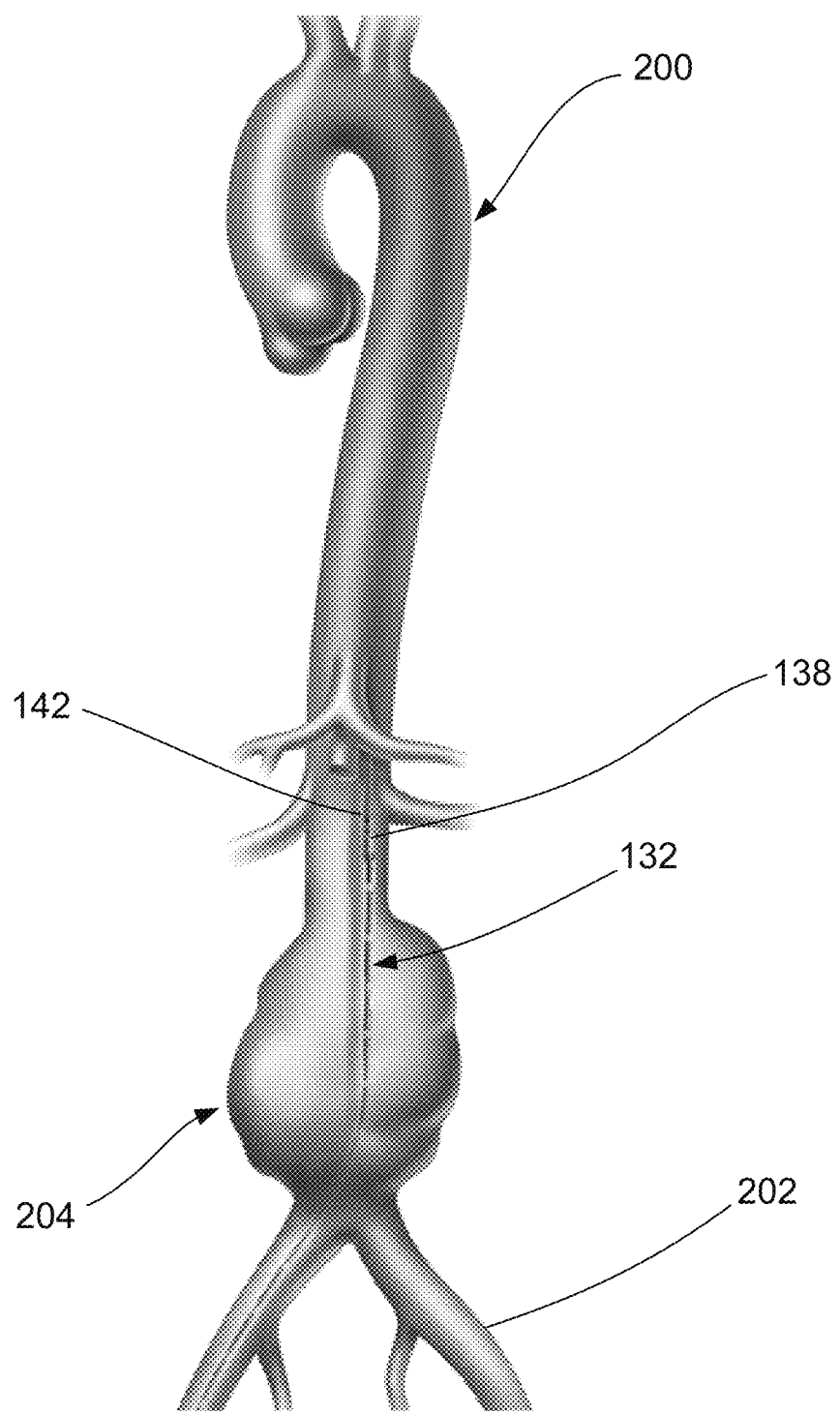
FIG. 7 is a side view of the aorta of FIG. 6 illustrating positioning of an imaging probe, as well as one or more sensors coupled thereto, for capturing data related to at least the stent graft and aortic wall.

FIG. 7 is a side view of the aorta 200 of FIG. 6 illustrating positioning of an imaging catheter 132 and imaging sensor 138 for capturing image data related to at least the stent graft 208 and aortic wall for providing at least flow visualization. Additionally, a functional measurement device 142 may be positioned on the imaging catheter 132 and may capture functional measurement data within the aorta 200. As described in greater detail herein, the image data, including flow visualization, and functional measurement data are then co-registered with extravascular image data, such as an angiogram, so as to provide the detection and further classification of endoleaks based on the co-registration. In one embodiment, systems of the present invention are configured to provide automated detection and classification of at least types I, II, III, and IV endoleaks based on the co-registered composite set of data, in accordance with methods described herein.

During a procedure, such as EVAR or TEVAR, a surgeon may perform a manual or automated pullback of the diagnostic probe 22 or imaging sensor 138, so as to capture image data and further visualize the aortic anatomy, as well as the stent graft 208 at the site of an abdominal aortic aneurysm (AAA) 204. Accordingly, the imaging sensor 138 is configured to capture image data (e.g., structure data and intravascular flow data) of the vessel during pullback.

With regard to the functional measurement data, any functional or physiological measurement is useful for practicing the invention. Exemplary physiological parameters include blood pressure or flow (velocity) inside the abdominal aorta within the vicinity of the stent graft. In certain aspects of the invention, these initial functional measurements may be further processed to determine other clinically relevant measurements, such as Fractional Flow reserve measurements, Coronary Flow reserve measurements, instantaneous wave-free ratio (iFR), combined P-V curves.

Coronary flow reserve is defined as the ratio of maximal coronary flow with hyperemia to normal flow. Coronary flow reserve signifies the ability of the myocardium to increase blood flow in response to maximal exercise. A ratio at or above 2 is considered normal. Abnormal CFR (a ratio below 2) indicates stenosis, abnormal constriction of microarteries, or both. Coronary flow reserve measures the velocity of the flow. Fractional flow reserve measure pressure differences across a portion of a vessel to determine whether a level of constriction or stenosis of the vessel will impede oxygen delivery to the heart muscle. Specifically, Fractional flow reserve is a ratio of a level of pressure distal to a portion of a vessel under examination to a level of pressure proximal to a portion of a vessel under examination. Often a cut-off point is 0.75 to 0.80 has been used, in which high values indicate a non-significant stenosis or constriction and lower values indicate a significant stenosis and lesion.

P-V loops provide a framework for understanding cardiac mechanics. Such loops can be generated by real time measurement of pressure and volume within the left ventricle. Several physiologically relevant hemodynamic parameters such as stroke volume, cardiac output, ejection fraction, myocardial contractility, etc. can be determined from these loops.

To generate a P-V loop for the left ventricle, the LV pressure is plotted against LV volume at multiple time points during a single cardiac cycle. The presence of a stenosis or constriction can alter the curve/shape of P-V loop from a normal P-V loop.

The instantaneous wave-free ratio (iFR) is a vasodilator-free pressure-only measure of the hemodynamic severity of a coronary stenosis comparable to fractional flow reserve (FFR) in diagnostic categorization.

It has been shown that distal pressure and velocity measurements, particularly regarding the pressure drop-velocity relationship such as Fractional Flow reserve (FFR), Coronary flow reserve (CFR), iFR, and combined P-V curves, reveal information about the stenosis severity and vessel closure. As contemplated by the invention, these parameters can also be used in the detection of endoleaks. For example, in use, a functional flow device may be advanced to a location relatively distal to an implanted stent-graft. The pressure and/or flow velocity may then be measured for a first time. Then, the device may be advanced to a location relatively proximal to the stent-graft and the pressure and/or flow is measured for a second time. The pressure and flow relationships at these two time points are then compared to assess the presence of endoleaks and provide improved guidance for any coronary interventions. The ability to take the pressure and flow measurements at the same location and same time with a combined pressure/flow guidewire, improves the accuracy of these pressure-velocity loops and therefore improves the accuracy of the diagnostic information.

Coronary flow reserve, Fractional flow reserve, iFR, and P-V loops may require measurements taken at different locations in the artery. In order to provide measurements for these parameters, systems and methods of the invention may assess pressure and flow at a first location of the data collector against a second location of the data collector within the vasculature. For example, a first location that is distal to a segment of a vessel under examination and a second location that is proximal to that segment of a vessel.

In order to obtain the physiological data described above, methods of the invention may involve the use of a functional measurement device. The functional measurement device may be equipped with a pressure sensor, a flow sensor, or any combination thereof. Exemplary functional measurement devices suitable for use in practicing the invention include FloWire Doppler Guidewire and the ComboWire XT Guidewire by Volcano Corporation.

The functional measurement device 23 of FIG. 1 and 142 of FIG. 7, for example, may include a pressure sensor. A pressure sensor allows one to obtain pressure measurements within a body lumen. Once the device is inside the vessel, the effectiveness of the EVAR procedure can be verified and the presence of endoleaks detected through the assessment of functional data. As discussed above, the sensing device 23, 142 can be maneuvered to a position relatively distal of the implanted stent graft. At this position, a first functional measurement is taken. The sensing device is then advanced to a position relatively proximal to the implanted stent graft 208 and a second functional measurement is taken. The appropriate distance away from the implanted stent graft 208 can be determined empirically and is within the ordinary skill of the art. In addition, the distal and proximal measurement positions are still within a limited space, i.e., the abdominal aorta 200, facilitating the identification of the positions. The two measurements can then be compared with a difference between the first and second measurements being indicative of an endoleak. For example, a drop in pressure near the vicinity of the stent graft 208 may indicate the presence of an endoleak. Because there is still a leak or opening in the stent graft allowing flow into the AAA after the EVAR procedure, the abdominal aorta 200 is unable to maintain pressure in the vicinity of the stent graft 208. In addition, an increase in flow may also indicate the presence of an endoleak. This is because blood is still flowing out the ineffectual seal made by the stent graft 208, which can be detected as an increase in flow.

The system described and illustrated in FIG. 1 is further configured to provide detection of at least one of a false lumen, mal-apposition, as well as graft enfolding and other features identifiable with gray-scale and color flow visualization, and further provide automatic identification of a site-of-interest with a potential endoleak. Furthermore, the system of FIG. 1 is further configured to automatically classify a detected endoleak as one of types I, II, III, or IV based on the co-registered sets of data, including the flow visualization data, intravascular image data, functional measurement data, and angiography. For example, in one embodiment, systems may be configured to detect mal-apposition and/or graft enfolding based on attributes of the lumen (e.g., dimensions of the aorta) before and after placement of the stent graft so as to determine if the endoleak is at the distal or proximal landing zone of the graft. Next, the system is configured to confirm leakage by cross-referencing color flow data, which may include motion detection. In turn, the system is configured to determine that the endoleak is a type IA (proximal) or type IB (distal) endoleak.

In the event that no mal-apposition and/or graft enfolding is detected, the system is configured to search image data for dual flow channels having different directions in the presence of the stent graft. In the event that dual flow channels having different directions are detected, the system is configured to determine that the endoleak is a type III endoleak. However, if the presence of a dual flow channel having different directions is detected in absence of a stent graft, the display 50, for example, is configured to provide a warning to the surgeon that there is possibly a dissection in the aortic wall, at which point the surgeon can act accordingly to prevent further bleeding and possible death.

In the event that no dual or multiple flow channels are detected from within the luminal surface of the aorta (or vessel of interest), the system is further configured to search image data for other flow channels and associated direction of flow. In the event that flow channels are detected at or near the outer rim of the AAA, the system is configured to determine that the endoleak is a type II endoleak.

In the event that no flow channels or mal-appositions are detected, the system is configured to search data for flow within the lumen or within the AAA (in absence of a stent graft) for areas with flow in the same direction without dual lumens, but with different flow rates and/or with "plaque" appearing within the lumen, which may be indicative of a thrombus.

As previously described, a system consistent with the present disclosure is configured to co-register the intravascular image data, extravascular image data, and functional measurement data. Image co-registration software provides the capability to co-register angiography, IVUS, and functional measurement data on one display with multiple views or displays with multiple views of the three dimensional volume around the physiology of interest.

Figure 8:
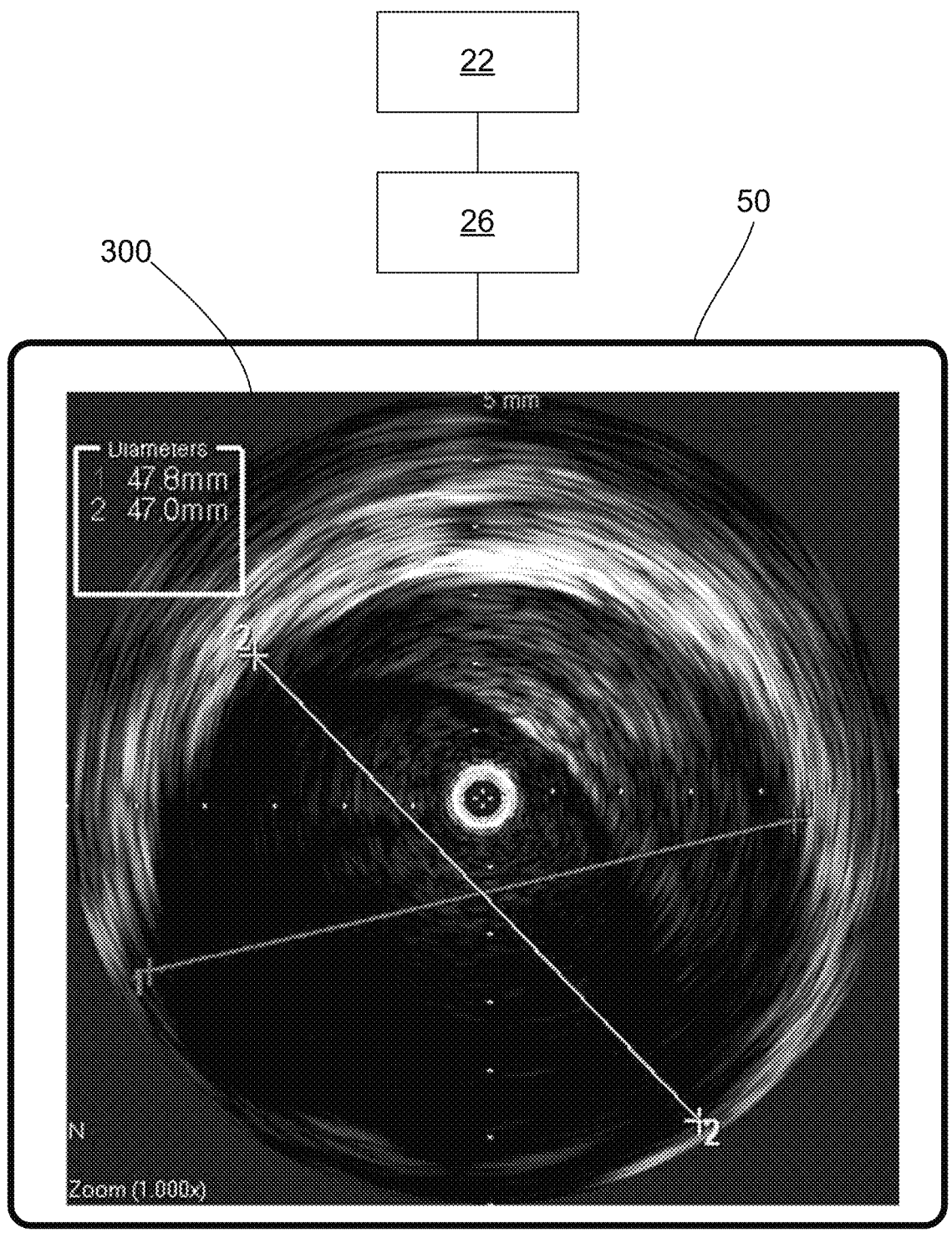
FIG. 8 is a block diagram illustrating the presentation of a cross-section of the aorta, including measured dimensions of the aorta, based on image data captured by an imaging catheter.
Figure 9:
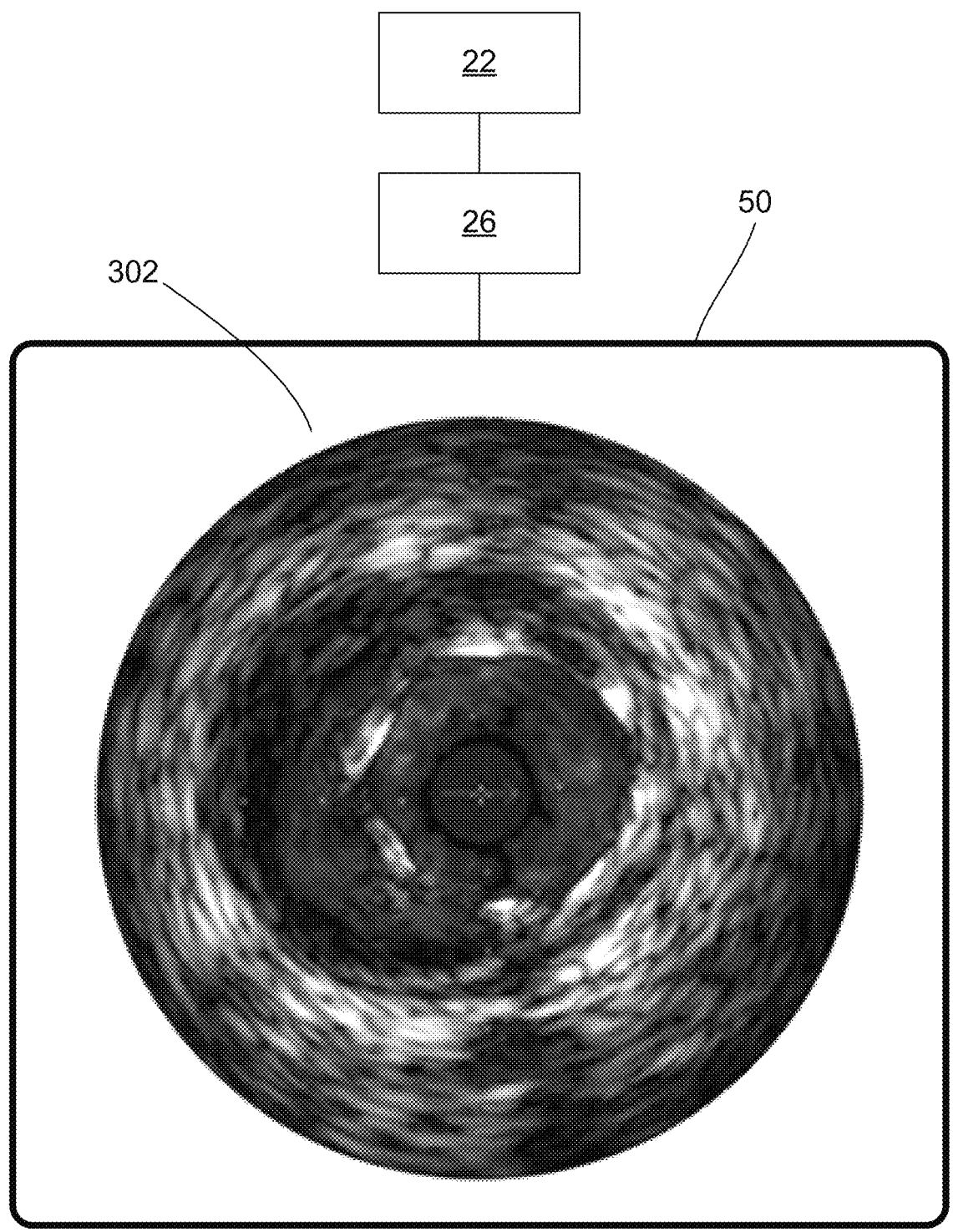
FIG. 9 is a block diagram illustrating the presentation of a cross-section of the aorta, including a flow characteristic of a fluid within the aorta, based on image data captured by an imaging catheter.
Figure 10:
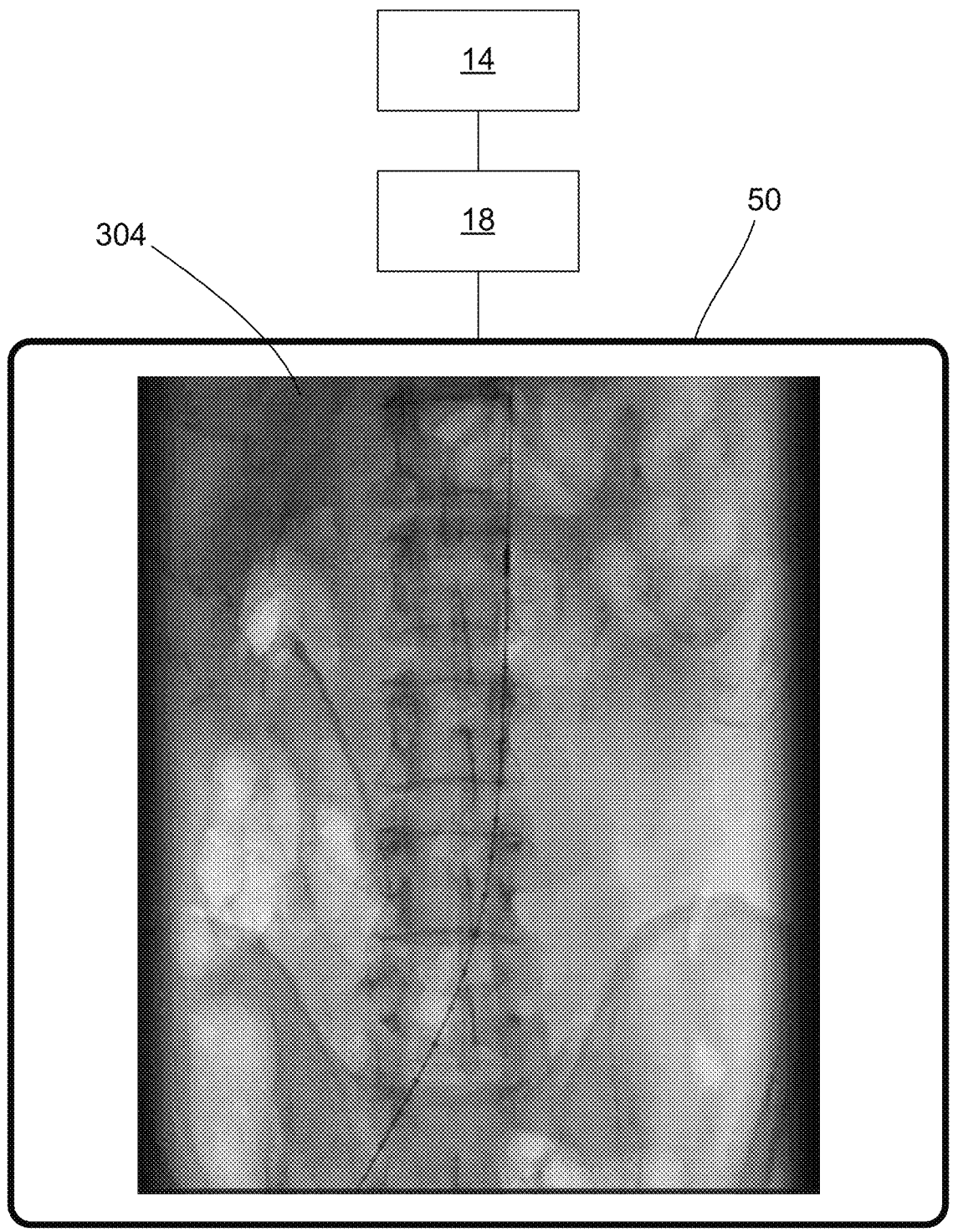
FIG. 10 is a block diagram illustrating the presentation of an angiogram of the aorta based on image data captured by an external imaging modality.
Figure 11:
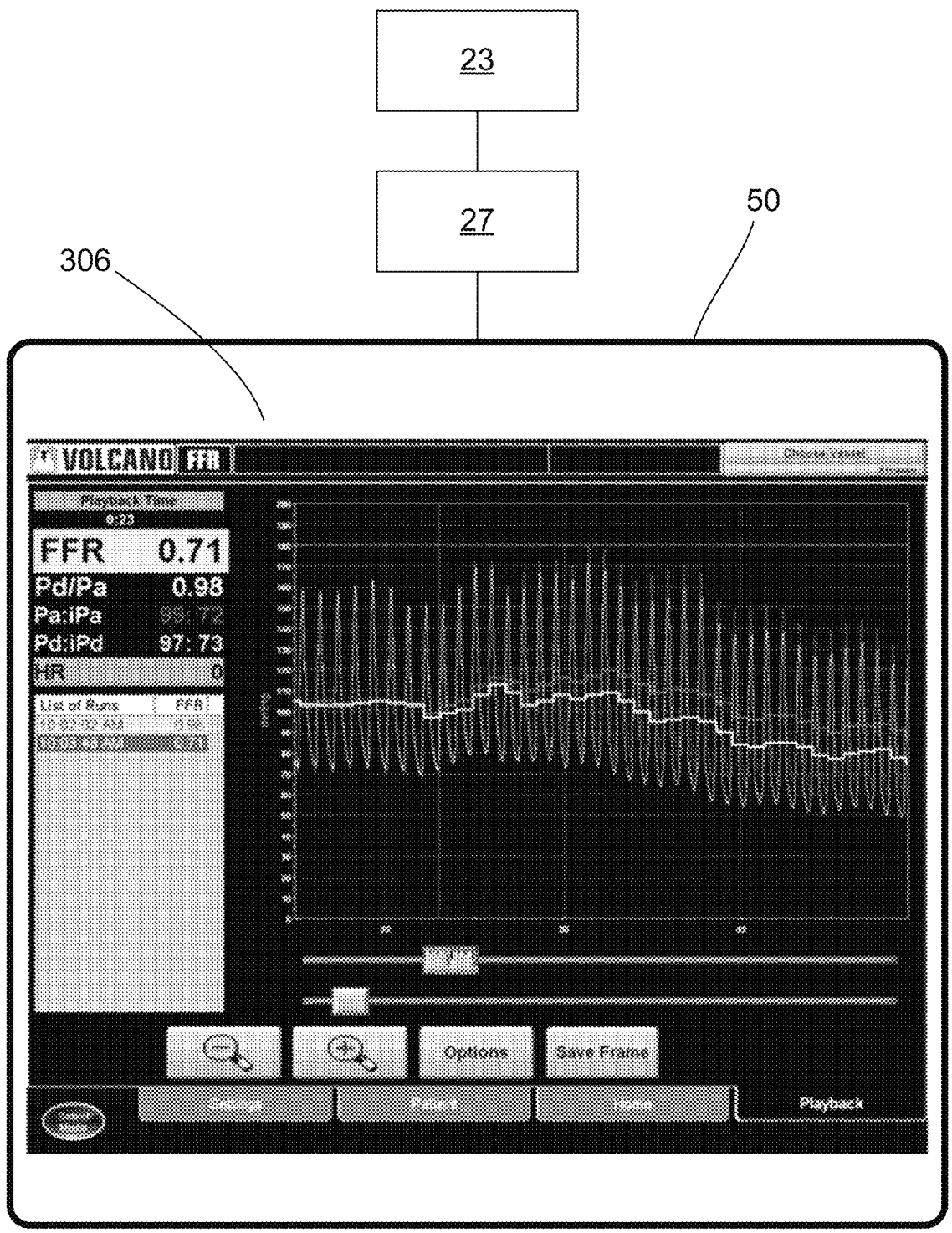
FIG. 11 is a block diagram illustrating the presentation of a graphical display of a Fractional Flow Reserve (FFR) determination of fluid within the aorta, based on functional measurement data captured by a sensor.
Figure 12:
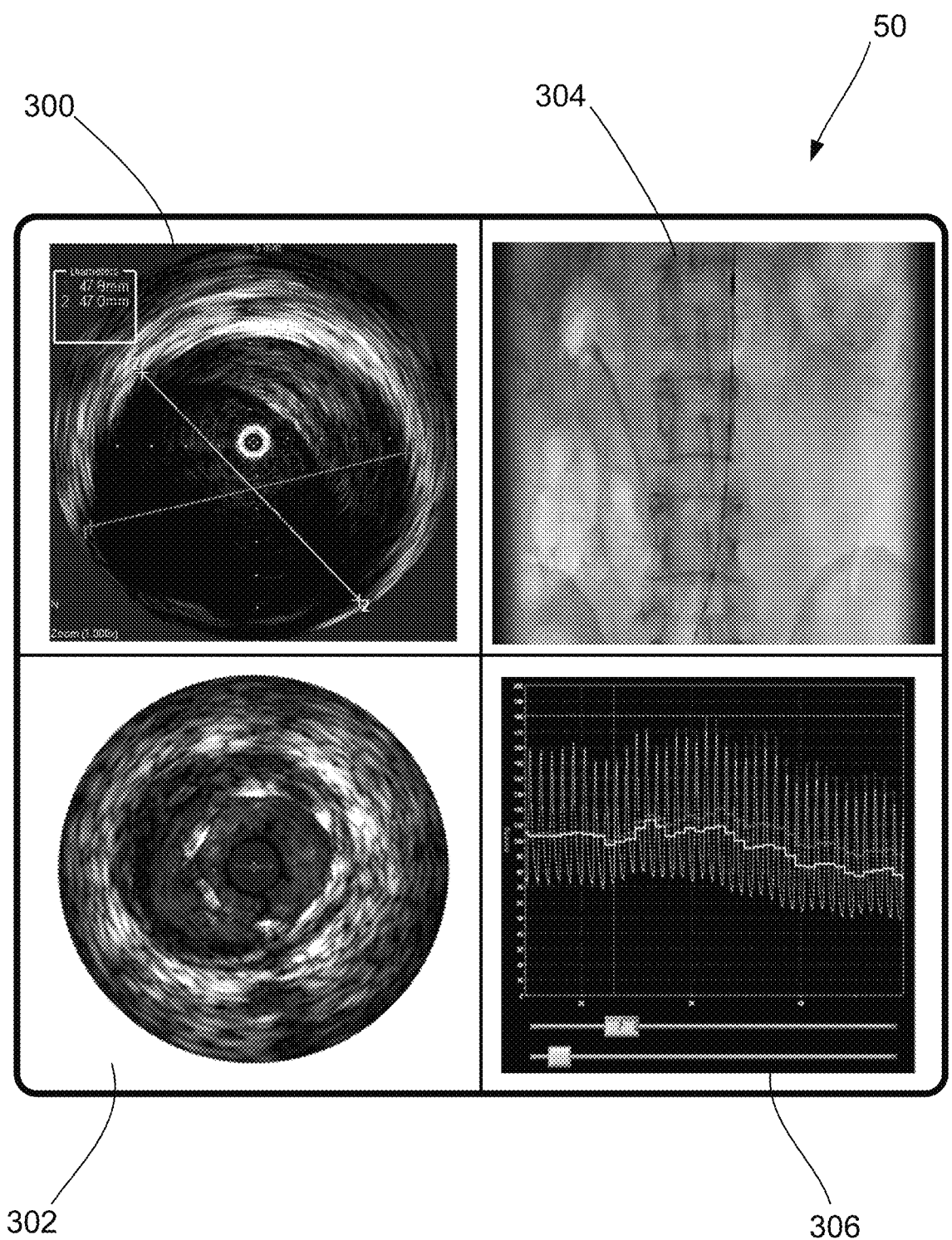
FIG. 12 illustrates co-registration and display of the data captured by the intra- and extraluminal data capturing modalities of FIGS. 8-11.

FIG. 8, for example, illustrates the presentation of a cross-section of the aorta on the display 50, including measured dimensions of the aorta, based on image data captured by an imaging catheter consistent with the present disclosure. In particular, FIG. 8 is a gray-scale IVUS image 300 of the aorta. FIG. 9 is a composite image 302 of flow data overlaid on the gray-scale image 300 of FIG. 8, thereby depicting a 360 degree cross-section view of the inside of the aorta, wherein the flow data represents blood flow in the aorta. The aligned image provides an additional level of detail to a physician that is not provided by an IVUS image alone. FIG. 10 illustrates the presentation of an angiogram 304 of the aorta on the display based on image data captured by the angiography device 14. FIG. 11 illustrates the presentation of a graphical display of a Fractional Flow Reserve (FFR) determination 308 of fluid within the aorta, based on functional measurement data captured by functional measurement device. FIG. 12 illustrates one display 50 with multiple views of the data captured by the intra- and extraluminal data capturing modalities of FIGS. 8-11. It should be appreciated that blood-vessel data can be used in a number of applications including, but not limited to, diagnosing and/or treating patients. For example, blood-vessel data can be used to identify and/or image blood vessel borders or boundaries, as provided by U.S. Pat. No. 6,381,350, which is incorporated by reference herein in its entirety. Another use for blood-vessel data is for classifying and/or imaging vascular plaque, as provided by U.S. Pat. No. 6,200,268, which is also incorporated by reference herein in its entirety. Another use for blood-vessel data is to classify vascular tissue, as provided by U.S. Pat. No. 8,449,465, which is also incorporated by reference herein in its entirety.

The system is configured to provide a composite map (3- or multi-dimensional) of the vessel including automatically detected areas of interest (e.g., high stress/strain maps, endoleaks, atherosclerosis, thrombus, dissection, etc.), particularly during an EVAR or TEVAR procedure. Additionally, the display co-registered composite data may be used for guidance during an EVAR/TEVAR procedure. For example, a surgeon may utilize the data to determine whether or not to treat the aneurysm (place the stent graft). The idea here is that in much the same way that we use the FFR data to determine whether to place a stent, a surgeon can rely on the IVUS and/or flow visualization to determine whether to place a graft. For example, IVUS can be used to determine the relative thickness of a section of a wall in the abdominal aorta. If the wall is too thin, it is likely to rupture, warranting a stent graft. To further confirm whether this is the case, data from a co-registered angiogram can be relied upon. In embodiment, after obtaining the above information related to placing of a stent graft, the surgeon may further be able to predict changes in aortic dimensions and/or pressure following stent graft placement.

Similarly, the co-registered composite sets of data can be used to when determining the optimal location for targeted drug delivery. Generally, the most ideal location within a vessel for drug delivery would be in a location where the vessel walls are thinnest.

Methods of the invention can further encompass treatment of the endoleak upon detection. Treatment will depend on the type of endoleak.

Type I leaks are generally treated as soon as detected. Extension cuffs or covered stents can be inserted at the leaking graft end to improve the seal, or embolization of the leak site with glue or coils can be used. Rarely, if detected intra-operatively during EVAR, conversion to an open procedure may be required if endovascular methods of sealing the leak are unsuccessful.

Type II leaks (retrograde flow through branch) usually spontaneously thrombose. As such at many institutions these leaks are not treated immediately; watchful waiting is employed and if the leak persists it is treated by embolising the branch vessel with glue or coils. Pre-emptive embolization of potential sources of collateral flow is sometimes performed prior to stent-graft insertion, particularly the internal iliac artery in select cases. Pre-emptive embolization of other branch vessels is controversial.

Type III leaks (graft mechanical failure) do not spontaneously resolve and are therefore treated immediately, usually with additional stent-graft components.

Type IV leaks (graft porosity) cannot be treated except by improving device selection.

Other embodiments are within the scope and spirit of the invention. For example, due to the nature of software, functions described above can be implemented using software, hardware, firmware, hardwiring, or combinations of any of these. Features implementing functions can also be physically located at various positions, including being distributed such that portions of functions are implemented at different physical locations. Steps of the invention may be performed using dedicated medical imaging hardware, general purpose computers, or both. As one skilled in the art would recognize as necessary or best-suited for performance of the methods of the invention, computer systems or machines of the invention include one or more processors (e.g., a central processing unit (CPU) a graphics processing unit (GPU) or both), a main memory and a static memory, which communicate with each other via a bus. A computer device generally includes memory coupled to a processor and operable via an input/output device.

Exemplary input/output devices include a video display unit (e.g., a liquid crystal display (LCD) or a cathode ray tube (CRT)). Computer systems or machines according to the invention can also include an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Memory according to the invention can include a machine-readable medium on which is stored one or more sets of instructions (e.g., software), data, or both embodying any one or more of the methodologies or functions described herein. The software may also reside, completely or at least partially, within the main memory and/or within the processor during execution thereof by the computer system, the main memory and the processor also constituting machine-readable media. The software may further be transmitted or received over a network via the network interface device.

While the machine-readable medium can in an exemplary embodiment be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any of the methodologies of the present invention. The term "machine-readable medium" shall accordingly be taken to include, but not be limited to, solid-state memories (e.g., subscriber identity module (SIM) card, secure digital card (SD card), micro SD card, or solid-state drive (SSD)), optical and magnetic media, and any other tangible storage media. Preferably, computer memory is a tangible, non-transitory medium, such as any of the foregoing, and may be operably coupled to a processor by a bus. Methods of the invention include writing data to memory—i.e., physically transforming arrangements of particles in computer memory so that the transformed tangible medium represents the tangible physical objects—e.g., the arterial plaque in a patient's vessel.

As used herein, the word "or" means "and or or", sometimes seen or referred to as "and/or", unless indicated otherwise.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A system for an aortic procedure, the system comprising:
    an imaging probe configured to capture intravascular image data from a longitudinal cross-section of an aorta;
    a sensor coupled to the imaging probe, wherein the sensor is configured to measure a fluid property within the longitudinal cross-section of the aorta; and
    a control system configured to co-register the intravascular image data and the fluid property and provide output representing the longitudinal cross-section of the aorta and a flow characteristic of a fluid therein, the control system further configured to detect an endoleak associated with an aortic repair procedure based on the co-registered image data and fluid property, and the control system further configured to classify the endoleak as one of a plurality of types of endoleaks based on the co-registered data.

2. The system of claim 1, wherein the control system is configured to compare the measured fluid property to an expected value to detect the endoleak.

3. The system of claim 2, wherein the expected value is obtained through use of the sensor.

4. The system of claim 1, wherein the control system is further configured to receive an angiogram including the aorta and to co-register the angiogram with the longitudinal cross-section of the aorta in the output.

5. The system of claim 4, wherein the output comprises a display that includes the longitudinal cross-section, the angiogram, the flow characteristic, and indicia showing at least one spatial relationship among the longitudinal cross-section, the angiogram, the flow characteristic.

6. The system of claim 4, wherein the display comprises a display that includes the longitudinal cross-section, the angiogram, and the flow characteristic, and further wherein the display depicts the spatial relationships among the longitudinal cross-section, the angiogram, the flow characteristic.

7. The system of claim 1, wherein the imaging probe comprises an intravascular ultrasound (IVUS) transducer.

8. The system of claim 7, wherein the imaging probe is configured to capture the intravascular image data via ultrasound at a frequency lower than 15 MHz.

9. The system of claim 8, wherein the frequency is between 9 MHz and 11 MHz and the characteristic of the flow that is depicted is velocity.

10. The system of claim 1, wherein the control system is configured to determine locations of parts of the aorta and the fluid in space and in time from the intravascular image data and the measurement, build a 4D model representing the aorta, and include the 4D model in the output.

11. A method for examining a large vessel, the method comprising:
    obtaining intravascular image data from a longitudinal cross-section of the vessel;
    obtaining measurement data of a property of a fluid within the vessel;
    co-registering, using a computer system, the intravascular image data with the measurement data;
    providing, using the computer system, an output depicting a feature of the longitudinal cross-section of the vessel and a characteristic of a flow of the fluid therein based on the co-registered image and measurement data;
    detecting, using the computer system, an endoleak associated with an aortic repair procedure based on the co-registered data; and classifying, using the computer system, the endoleak as one of a plurality of types of endoleaks based on the co-registered data.

12. The method of claim 11, wherein detecting the endoleak comprises comparing the measurement to an expected measure.

13. The method of claim 11, wherein the vessel is an aorta, the method further comprising:
obtaining an angiographic image that includes the aorta; and
including the angiographic image in the output.

14. The method of claim 13, further comprising displaying the intravascular image, the angiographic image, the characteristic of the flow, and markers showing at least one spatial relationship among the intravascular image, the angiographic image, and the characteristic of the flow.

15. The method of claim 13, further comprising:
displaying the intravascular image, the angiographic image, and the characteristic of the flow; and
depicting the spatial relationships among the intravascular image, the angiographic image, and the characteristic of the flow.

16. The method of claim 11, wherein the vessel is an aorta obtaining the intravascular image data comprises performing an intravascular ultrasound operation within the aorta.

17. The method of claim 16, further comprising performing the ultrasound operation at a frequency lower than 15 MHz.

18. The method of claim 17, wherein the frequency is between 9 MHz and 11 MHz and the characteristic of the flow is velocity.

* * * * *